(12) United States Patent
Willhite et al.

(10) Patent No.: US 10,321,929 B2
(45) Date of Patent: Jun. 18, 2019

(54) APPARATUS AND METHOD FOR CUTTING TISSUE

(71) Applicant: Gyrus ACMI, Inc., Southborough, MA (US)

(72) Inventors: Joel A. Willhite, Memphis, TN (US); Kevin C. Edwards, Olive Branch, MS (US)

(73) Assignee: Gyrus ACMI, Inc., Southborough, MA (US)

( * ) Notice: Subject to any disclaimer, the term of this patent is extended or adjusted under 35 U.S.C. 154(b) by 106 days.

(21) Appl. No.: 14/706,041

(22) Filed: May 7, 2015

(65) Prior Publication Data

US 2015/0327881 A1 Nov. 19, 2015

Related U.S. Application Data

(60) Provisional application No. 61/994,293, filed on May 16, 2014.

(51) Int. Cl.
*A61B 17/32* (2006.01)
*A61B 17/3205* (2006.01)

(52) U.S. Cl.
CPC .... *A61B 17/32002* (2013.01); *A61B 17/3205* (2013.01); *A61B 2017/320032* (2013.01); *A61B 2217/005* (2013.01)

(58) Field of Classification Search
CPC ............... A61B 17/32002; A61B 17/3205
See application file for complete search history.

(56) References Cited

U.S. PATENT DOCUMENTS

| | | | |
|---|---|---|---|
| 4,014,342 A | | 3/1977 | Staub et al. |
| 4,167,944 A | | 9/1979 | Banko |
| 4,203,444 A | | 5/1980 | Bonnell et al. |
| 4,274,414 A | | 6/1981 | Johnson et al. |
| 4,649,919 A | | 3/1987 | Thimsen et al. |
| 4,735,605 A | * | 4/1988 | Swartz ............ A61B 17/32002 30/29.5 |
| 4,792,327 A | | 12/1988 | Swartz |
| 4,811,734 A | * | 3/1989 | McGurk-Burleson ...... A61B 17/32002 30/240 |
| 4,844,064 A | | 7/1989 | Thimsen et al. |
| 4,850,354 A | * | 7/1989 | McGurk-Burleson ...... A61B 17/32002 606/170 |
| 4,867,157 A | * | 9/1989 | McGurk-Burleson ...... A61B 17/32002 606/170 |
| 4,932,935 A | | 6/1990 | Swartz |
| 5,074,841 A | | 12/1991 | Ademovic et al. |

(Continued)

FOREIGN PATENT DOCUMENTS

WO    WO 92/07500    5/1992

*Primary Examiner* — Richard G Louis
(74) *Attorney, Agent, or Firm* — Pandiscio & Pandiscio (57) ABSTRACT

A cutting instrument comprising: an outer tube; an inner tube rotatably disposed within the outer tube; the inner tube comprising an opening having a leading edge and a trailing edge; and the outer tube comprising a window having a leading edge and a trailing edge; at least one of the leading edge of the opening, the trailing edge of the opening, the leading edge of the window and the trailing edge of the window comprising a canted edge; and the window of the outer tube being adapted to be completely blocked by the inner tube during a phase of the rotation of the inner tube within the outer tube.

20 Claims, 12 Drawing Sheets

(56) References Cited

U.S. PATENT DOCUMENTS

| | | | |
|---|---|---|---|
| 5,242,460 | A | 9/1993 | Klein et al. |
| 5,403,334 | A | 4/1995 | Evans et al. |
| 5,693,063 | A | 12/1997 | Van Wyk et al. |
| 6,024,751 | A | 2/2000 | Lovato et al. |
| 6,053,923 | A | 4/2000 | Veca et al. |
| 6,309,399 | B1 | 10/2001 | Barbut et al. |
| 6,530,891 | B2 | 3/2003 | Miller |
| 8,585,274 | B2 | 11/2013 | Householder et al. |
| 8,608,666 | B2 | 12/2013 | Sjostrom |
| 8,876,731 | B2 | 11/2014 | Sjostrom |
| 2002/0077646 | A1 | 6/2002 | Truwit et al. |
| 2003/0229293 | A1 | 12/2003 | Hibner et al. |
| 2004/0167427 | A1 | 8/2004 | Quick et al. |
| 2005/0065538 | A1 | 3/2005 | Van Wyk |
| 2006/0178670 | A1 | 8/2006 | Woloszko et al. |
| 2006/0196038 | A1 | 9/2006 | Van Wyk |
| 2008/0249553 | A1 | 10/2008 | Gruber et al. |
| 2009/0234378 | A1* | 9/2009 | Escudero ......... A61B 17/32075 606/180 |

* cited by examiner

APPARATUS AND METHOD FOR CUTTING TISSUE

REFERENCE TO PENDING PRIOR PATENT APPLICATION

This patent application claims benefit of prior U.S. Provisional Patent Application Ser. No. 61/994,293, filed May 16, 2014 by Gyrus ACMI, Inc. (d.b.a. Olympus Surgical Technologies America) and Joel A. Willhite et al. for APPARATUS AND METHOD FOR CUTTING TISSUE, which patent application is hereby incorporated herein by reference.

FIELD OF THE INVENTION

This invention relates to surgical apparatus and methods in general, and more particularly to surgical apparatus and methods for cutting tissue.

BACKGROUND OF THE INVENTION

In many situations, tissue may need to be accessed at a remote surgical site, excised from the adjacent anatomy and then the excised tissue removed from the remote surgical site. By way of example but not limitation, during arthroscopic surgery, endoscopic surgery, ENT surgery, etc., relatively small visualization devices (e.g., "scopes") and relatively small surgical tools (e.g., graspers, cutters, cauterizers, etc.) are generally introduced into a restricted space within the human body (e.g., the interior of a joint, the interior of the abdomen, the interior of a nasal passage, etc.) and then used at that location for a specific surgical procedure (e.g., to trim meniscal cartilage in a joint, to excise a tissue mass in the abdomen, to excise a tissue mass in a nasal passage, etc.). In many such surgeries, fluid is introduced into the surgical site (and thereafter removed from the surgical site) so as to distend the anatomy for better access and/or visualization (e.g., so as to distend the knee joint for better access and/or visualization), and/or to improve visibility (e.g., so as to flush away blood), and/or to remove debris (e.g., so as to remove severed tissue by suction).

One of the surgical tools frequently employed in such surgeries is the so-called "powered shaver". Powered shavers typically comprise an outer tube having a window, and an inner tube rotatably disposed within the outer tube and having an opening, wherein rotation of the inner tube within the outer tube causes the opening of the inner tube to repetitively sweep across the window of the outer tube, whereby to shear off tissue extending into the window of the outer tube. Suction is applied to the interior of the inner tube so as to remove the tissue sheared off by the powered shaver. See, for example, U.S. Pat. No. 4,203,444 (Bonnell et al.) and U.S. Pat. No. 4,867,157 (McGurk-Burleson et al.).

Unfortunately, current powered shavers tend to suffer from one or more disadvantages. By way of example but not limitation, current powered shavers tend to suffer from small window sizes, which is generally the result of efforts to ensure adequate suction in order to remove sizable debris through the interior of the inner tube. In addition, current powered shavers tend to suffer from inefficient cutting action, which is generally the result of the shearing geometries employed. Among other things, with current powered shavers, the oscillating motion and location of the cutting surfaces tend to "bat" tissue around, in a side-to-side motion. Furthermore, current powered shavers tend to suffer from poor suction, which is generally the result of the geometries used for the window of the outer tube and the opening in the inner tube.

Thus it would be advantageous to provide a new powered cutter which improves upon the deficiencies of the prior art. Among other things, it would be advantageous to provide a new powered cutter which provides enlarged window sizes, improved cutting action and superior suction.

SUMMARY OF THE INVENTION

The present invention comprises the provision and use of a new powered cutter which improves upon the deficiencies of the prior art. Among other things, the new powered cutter provides enlarged window sizes, improved cutting action and superior suction.

In one form of the invention, there is provided a cutting instrument comprising:
an outer tube;
an inner tube rotatably disposed within said outer tube;
said inner tube comprising an opening having a leading edge and a trailing edge; and
said outer tube comprising a window having a leading edge and a trailing edge;
at least one of said leading edge of said opening, said trailing edge of said opening, said leading edge of said window and said trailing edge of said window comprising a canted edge; and
said window of said outer tube being adapted to be completely blocked by said inner tube during a phase of the rotation of said inner tube within said outer tube.

In another form of the invention, there is provided a cutting instrument comprising:
an outer tube;
an inner tube rotatably disposed within said outer tube;
said inner tube comprising an opening having a leading edge and a trailing edge; and
said outer tube comprising a window having a leading edge and a trailing edge;
at least one of said leading edge of said opening and said trailing edge of said opening comprising a canted edge, and at least one of said leading edge of said window and said trailing edge of said window comprising a canted edge; and
wherein said at least one canted edge of said opening and said at least one canted edge of said window are canted in the same direction of turn.

In another form of the invention, there is provided a method for cutting an object, the method comprising:
providing a cutting instrument comprising:
an outer tube;
an inner tube rotatably disposed within said outer tube;
said inner tube comprising an opening having a leading edge and a trailing edge; and
said outer tube comprising a window having a leading edge and a trailing edge;
at least one of said leading edge of said opening, said trailing edge of said opening, said leading edge of said window and said trailing edge of said window comprising a canted edge; and
said window of said outer tube being adapted to be completely blocked by said inner tube during a phase of the rotation of said inner tube within said outer tube;
positioning the object in said window; and
rotating said inner tube within said outer tube.

In another form of the invention, there is provided a method for cutting an object, the method comprising:
providing cutting instrument comprising:

an outer tube;
an inner tube rotatably disposed within said outer tube;
said inner tube comprising an opening having a leading edge and a trailing edge; and
said outer tube comprising a window having a leading edge and a trailing edge;
at least one of said leading edge of said opening and said trailing edge of said opening comprising a canted edge, and at least one of said leading edge of said window and said trailing edge of said window comprising a canted edge; and
wherein said at least one canted edge of said opening and said at least one canted edge of said window are canted in the same direction of turn;
positioning the object in said window; and
rotating said inner tube within said outer tube.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

The present invention comprises the provision and use of a new powered cutter which improves upon the deficiencies of the prior art. Among other things, this new powered cutter provides enlarged window sizes, improved cutting action and superior suction.

Figure 1:
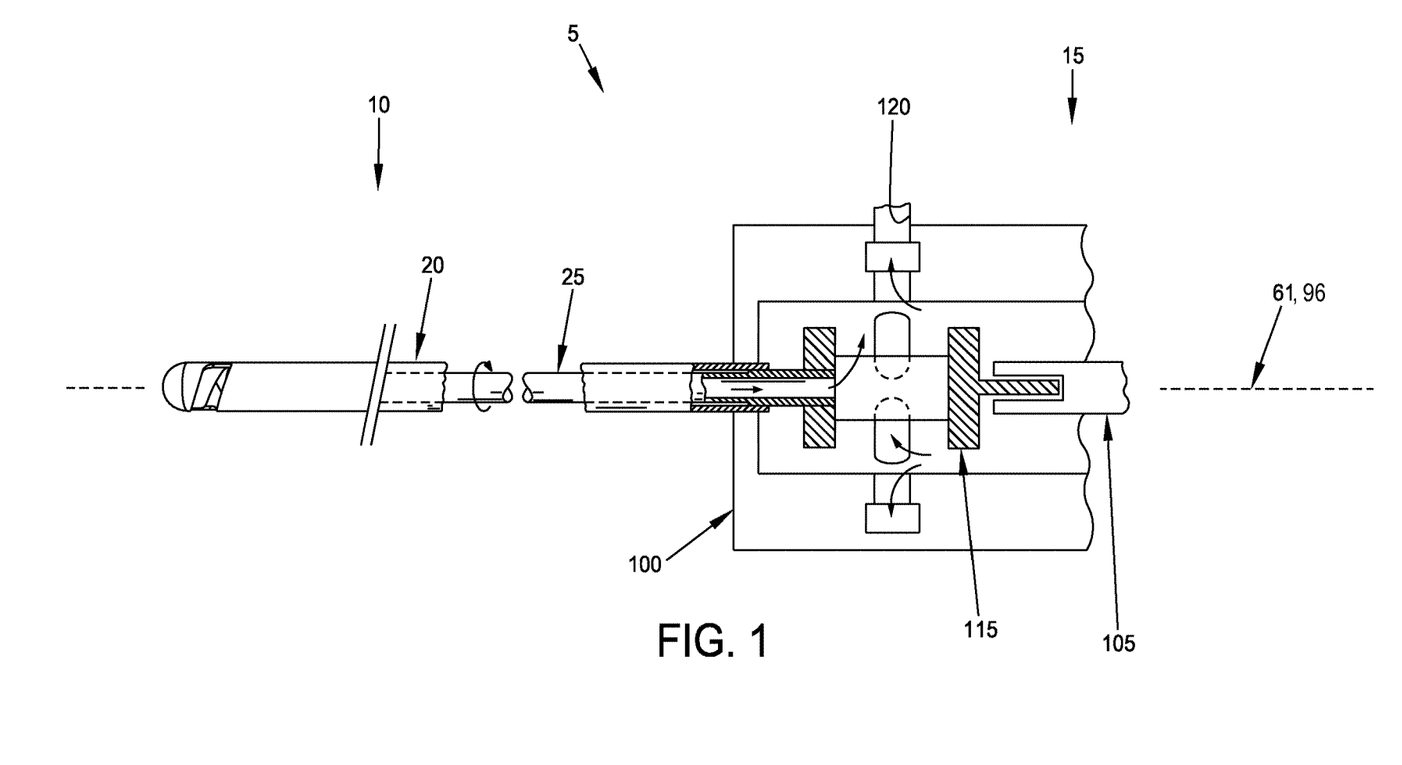
FIG. 1 is a schematic view showing a novel powered cutter formed in accordance with the present invention.
Figure 2:
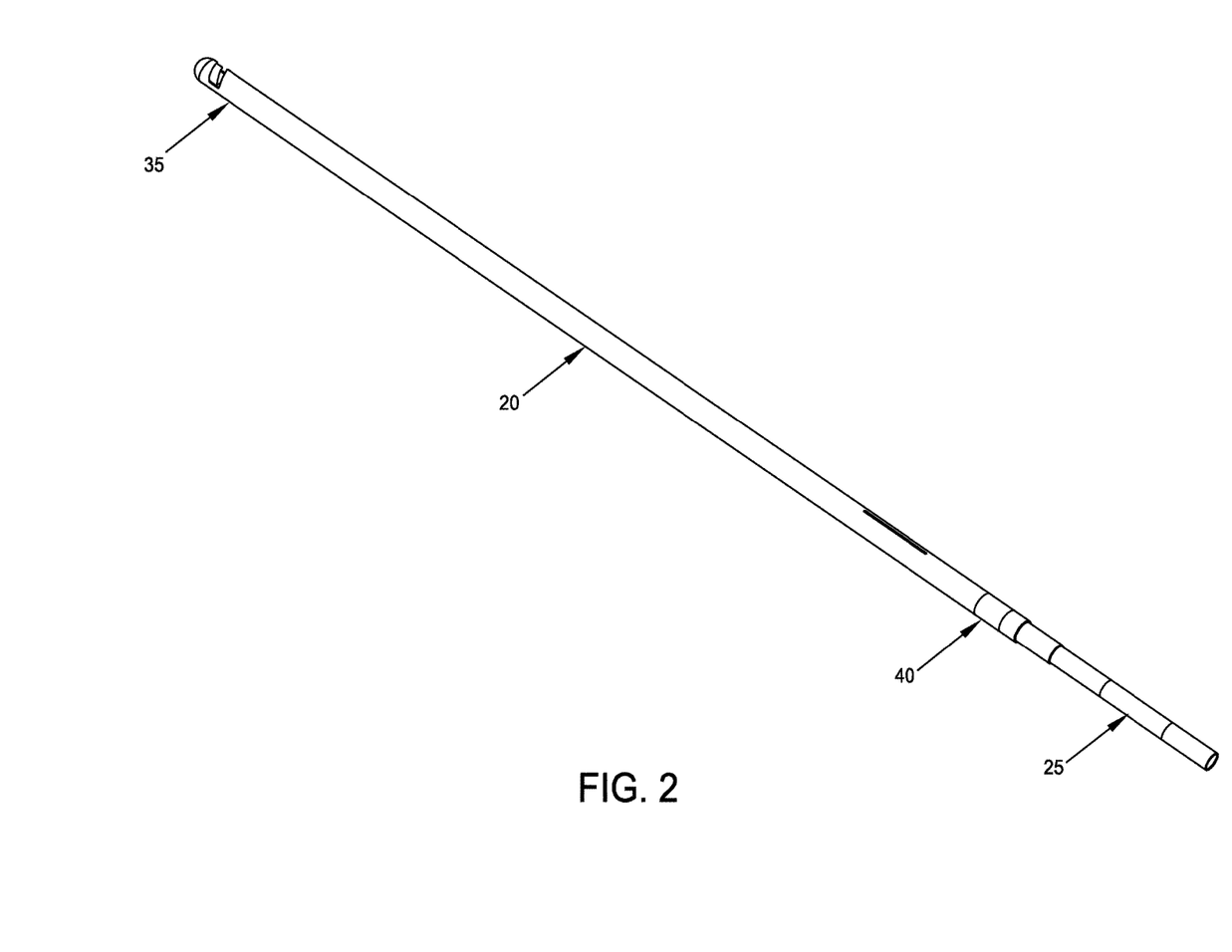
FIGS. 2-5 are schematic views showing the blade assembly of the powered cutter shown in FIG. 1.
Figure 3:
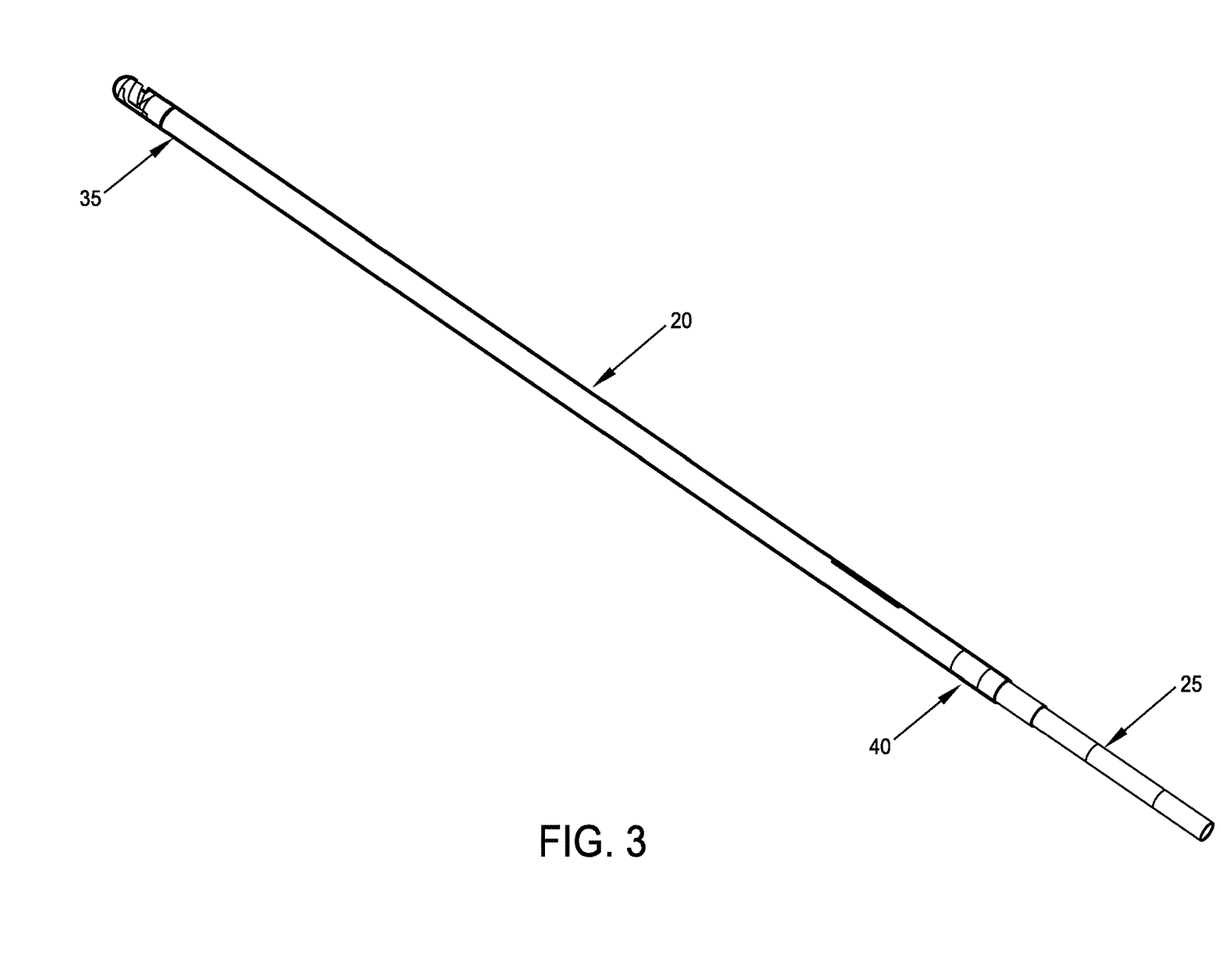
Figure 4:
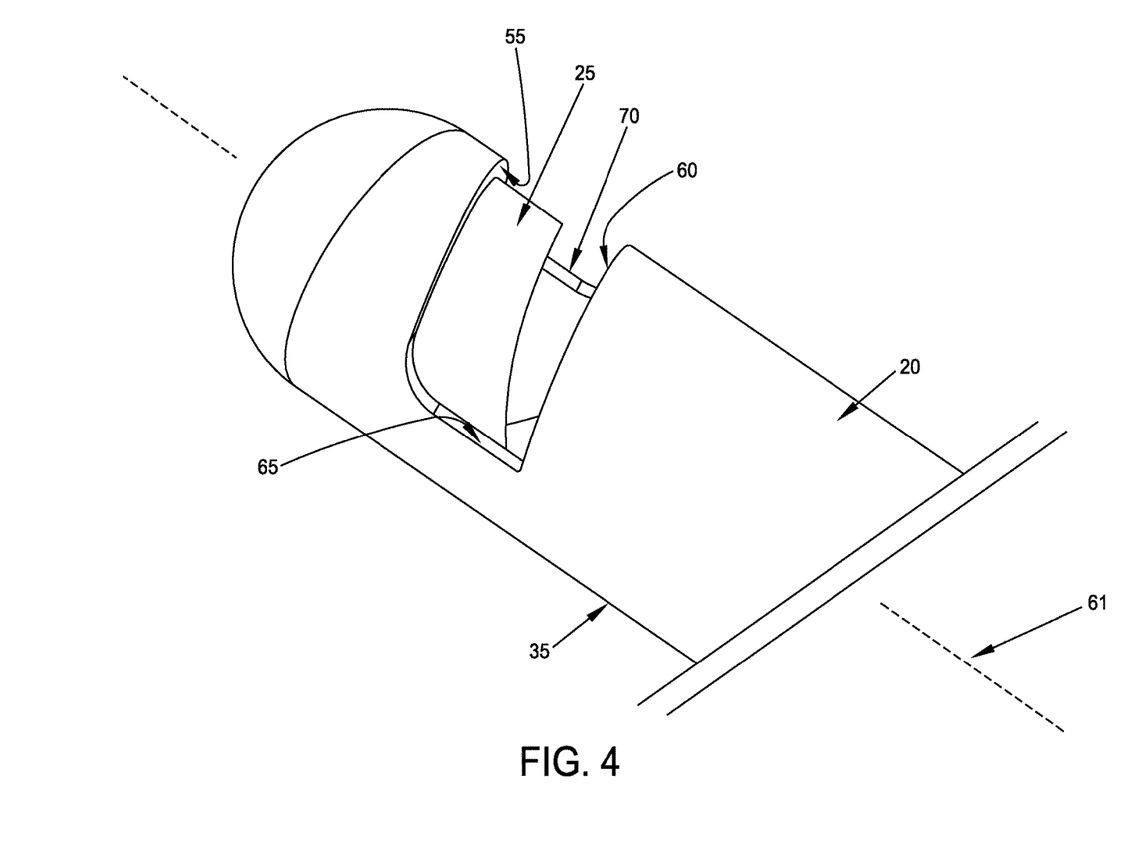
Figure 5:
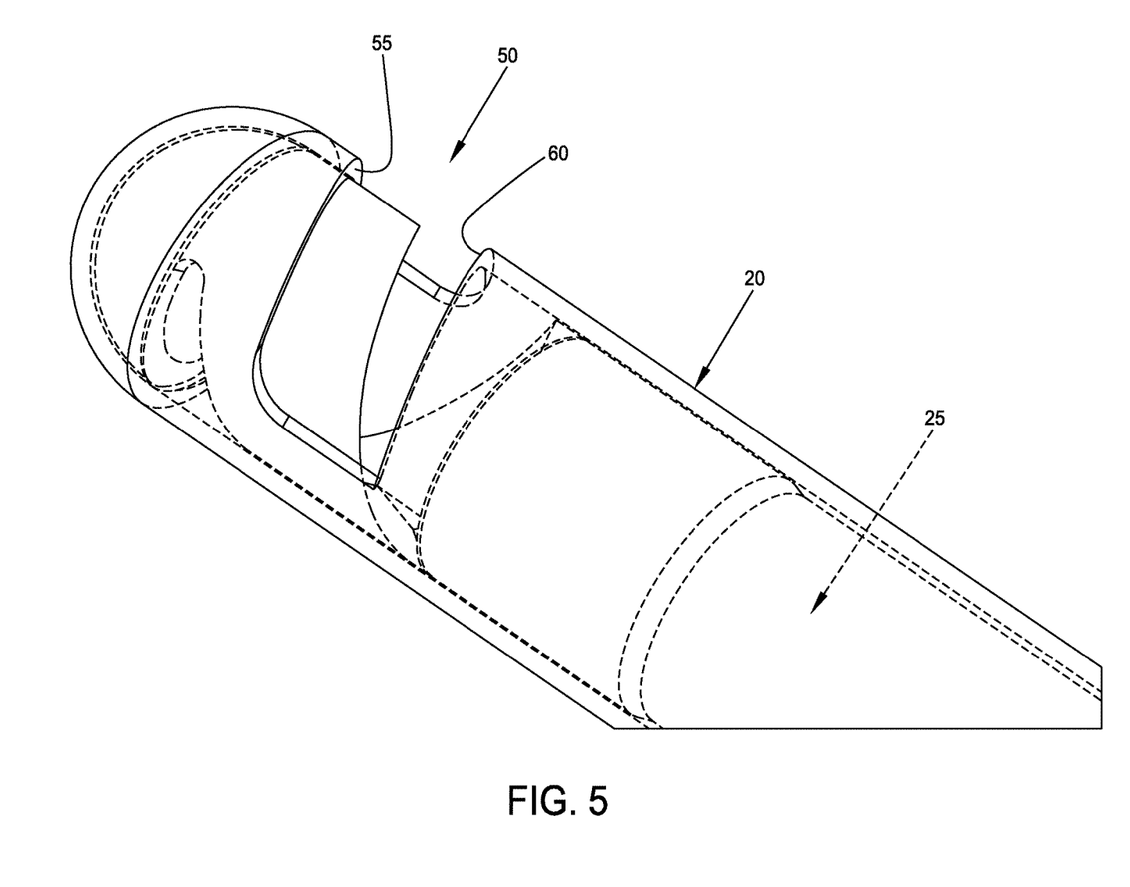

More particularly, and looking now at FIG. 1, there is shown a novel powered cutter 5 formed in accordance with the present invention. Novel powered cutter 5 generally comprises a blade assembly 10 and a handle assembly 15. As will hereinafter be discussed in further detail, blade assembly 10 is intended to be mated to handle assembly 15 (or another handle assembly) at the time of use, and detached from handle assembly 15 (or another handle assembly) after use (e.g., for cleaning and sterilization, repair or replacement, etc.). Alternatively, blade assembly 10 may be mated to handle assembly 15 (or another handle assembly) at the time of manufacture, e.g., such as in the case of a one-piece disposable system.

Blade assembly 10 is shown in greater detail in FIGS. 1-5. Blade assembly 10 generally comprises an outer tube 20 and inner tube 25 rotatably disposed within outer tube 20.

Outer tube 20 is shown in greater detail in FIGS. 1-6. Outer tube 20 generally comprises a distal end 35, a proximal end 40, and a lumen 45 extending from distal end 35 to proximal end 40. In one preferred form the present invention, outer tube 20 preferably comprises a closed distal end 48.

Figure 6:
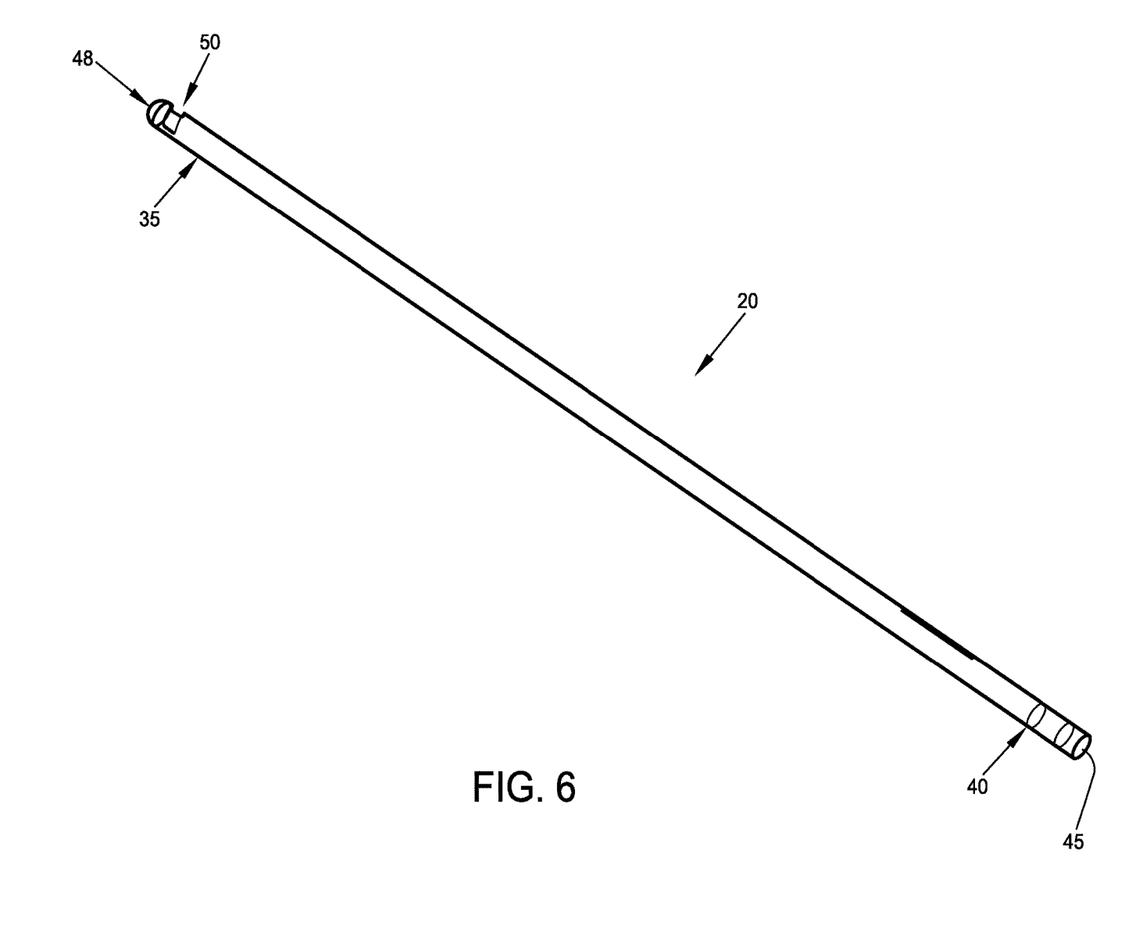
FIG. 6 is a schematic view showing the outer tube of the blade assembly shown in FIGS. 2-5.

Outer tube 20 comprises a window 50 comprising a leading edge 55 and a trailing edge 60. In one preferred form of the invention, leading edge 55 and trailing edge 60 are canted relative to the longitudinal axis 61 of outer tube 20. In one preferred form of the invention, leading edge 55 and trailing edge 60 have a helical configuration (which may be of constant pitch or non-constant pitch). In another preferred form of the invention, leading edge 55 and trailing edge 60 have a configuration which is a segment of an ellipse. In one preferred form of the present invention, outer tube 20 also comprises a first edge 65 connecting leading edge 55 to trailing edge 60, and a second edge 70 connecting leading edge 55 to trailing edge 60. In one preferred form of the invention, leading edge 55, trailing edge 60, first edge 65 and second edge 70 form a prismatic section of a parallelogram.

Inner tube 25 is shown in greater detail in FIGS. 1-5 and 7-9. Inner tube 25 generally comprises a distal end 75, a proximal end 80, and a lumen 83 extending from distal end 75 to proximal end 80. In one preferred form of the present invention, inner tube 25 preferably comprises a closed distal end 84.

Figure 7:
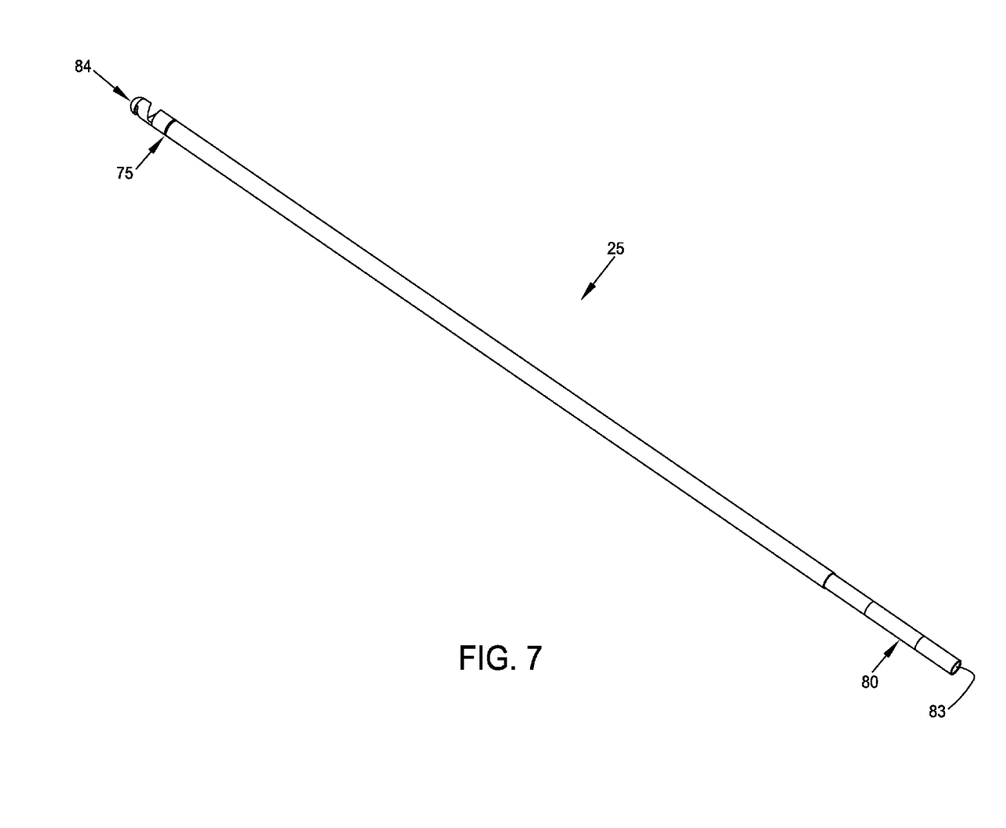
FIGS. 7-9 are schematic views showing the inner tube of the blade assembly shown in FIGS. 2-5.
Figure 8:
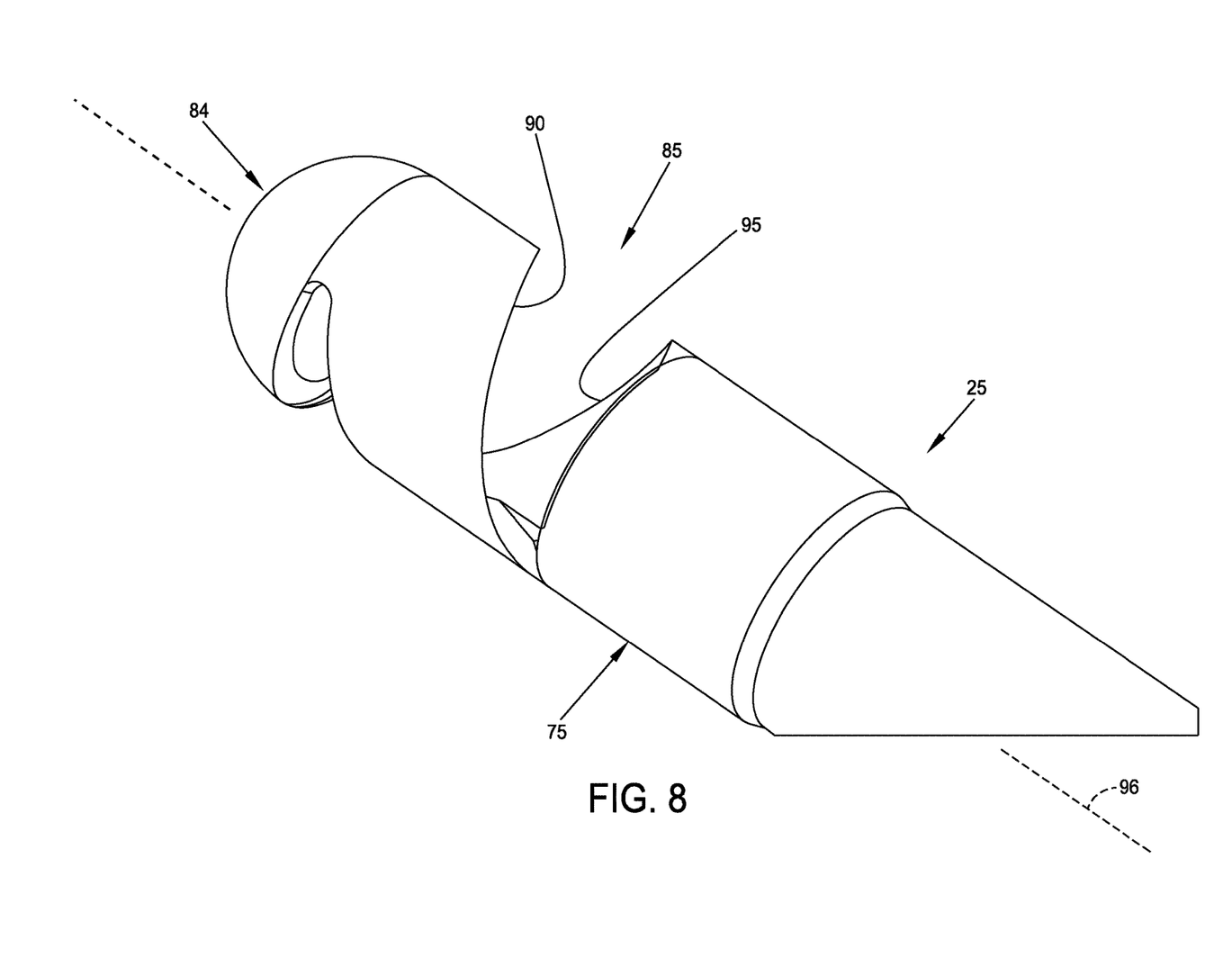
Figure 9:
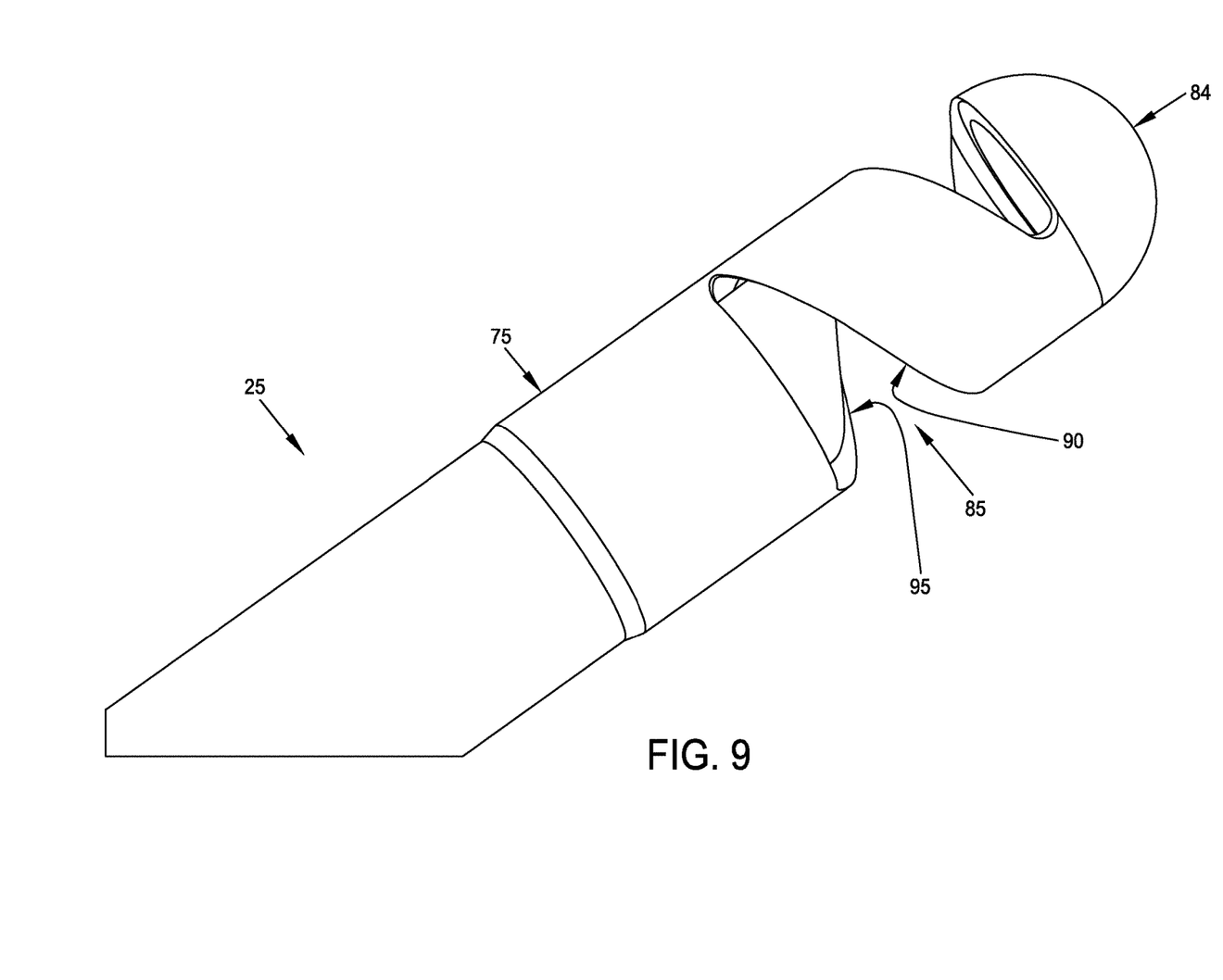

Inner tube 25 comprises an opening 85 comprising a leading edge 90 and a trailing edge 95. In one preferred form of the invention, leading edge 90 and trailing edge 95 are canted relative to the longitudinal axis 96 of inner tube 25. In one preferred form of the invention, leading edge 90 and trailing edge 95 have a helical configuration (which may be of constant pitch or non-constant pitch). In another preferred form of the invention, leading edge 90 and trailing edge 95 have a configuration which is a segment of an ellipse.

It should be appreciated that leading edge 90 of inner tube 25 extends at an angle to trailing edge 60 of outer tube 20, and/or trailing edge 95 of inner tube 25 extends at an angle to leading edge 55 of outer tube 20, so as to create a shearing action between such surfaces (i.e., edges) when inner tube 25 is rotated relative to outer tube 20, as will hereinafter be discussed.

Inner tube 25 is rotatably disposed within outer tube 20 such that rotation of inner tube 25 within outer tube 20 causes opening 85 of inner tube 25 to repetitively sweep across window 50 of outer tube 20, whereby to shear off tissue extending into window 50 of outer tube 20. More particularly, in accordance with the present invention, as inner tube 25 is rotated within outer tube 20, leading edge 90 of inner tube 25 is swept across trailing edge 60 of outer tube 20 or, depending on the direction of rotation of inner tube 25 relative to outer tube 20, trailing edge 95 of inner tube 25 is swept across leading edge 55 of outer tube 20, so as to create a shearing action at the interface of leading edge 90 of inner tube 25 and trailing edge 60 of outer tube 20, or at the interface of trailing edge 95 of inner tube 25 and leading edge 55 of outer tube 20. This shearing action serves to cut away tissue extending into window 50 of outer tube 20. It should be appreciated that this shearing action is superior to the cutting action of conventional powered cutters due to the moving point contact of the shearing ("scissoring") surfaces (i.e., edges). In addition, this shearing action is superior to the cutting action of conventional powered cutters, inasmuch as the cutting forces of novel powered cutter 5 are generally directed proximally or distally, rather than laterally (as is the case where the side edges of windows are used for cutting). Directing the cutting forces proximally or distally, rather than laterally, can help the surgeon keep the powered cutter in the desired position and also help keep tissue from being "batted" around, in a side-to-side motion, during cutting. Suction applied to lumen 83 of inner tube 25 removes the excised tissue from blade assembly 10.

If desired, space can be provided between inner tube 25 and outer tube 20 so as to allow irrigation to be supplied to the surgical site.

In one preferred form of the invention, inner tube 25 is configured to completely block window 50 of outer tube 20 during a phase of the rotation of inner tube 25 within outer tube 20. As a result, larger window sizes can be used while still providing superior suction for the blade assembly.

Figure 10A:
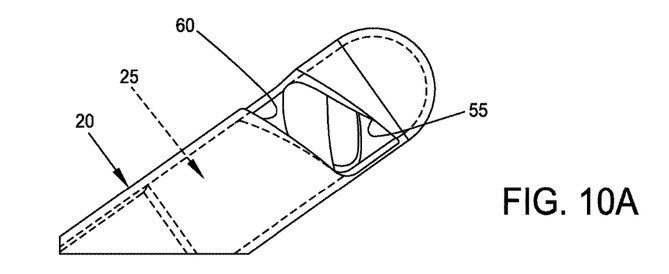
FIGS. 10A-10C are schematic views showing the blade assembly in different states of operation.
Figure 10B:
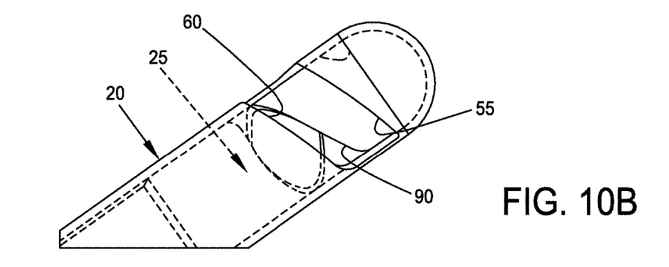
Figure 10C:
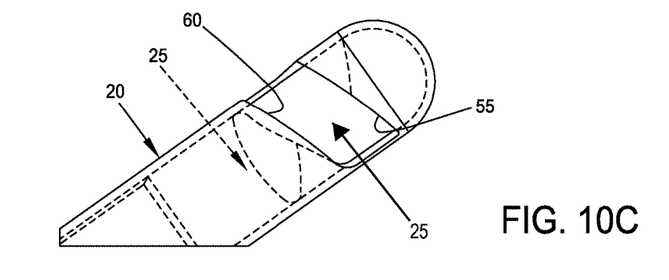

In one preferred form of the invention, and looking now at FIGS. 10A, 10B and 10C, blade assembly 10 can be considered to assume three different "states" as inner tube 25 rotates within outer tube 20, i.e., a "window fully open" state (FIG. 10A) where suction is used to facilitate tissue engagement, a "resecting" state (FIG. 10B) where the surfaces (i.e., edges) of inner tube 25 and outer tube 20 cooperate to provide a scissoring action so as to cut tissue extending into window 50 of outer tube 20, and a "window fully closed" state (FIG. 10C) where inner tube 25 substantially completely closes off window 50 of outer tube 20, thereby allowing for maximum inner lumen suction to rid the cutting area of tissue and fluid.

As shown in FIG. 1, blade assembly 10 is intended to be mated to handle assembly 15 (or another handle assembly) at the time of use, and detached from handle assembly 15 (or another handle assembly) after use (e.g., for cleaning and sterilization, repair or replacement, etc.). Alternatively, blade assembly 10 may be mated to handle assembly 15 (or another handle assembly) at the time of manufacture, e.g., such as in the case of a one-piece disposable system. Handle assembly 15 is provided with a housing 100 for securely mounting the distal end 40 of outer tube 20, and means for coupling a drive shaft 105 to inner tube 25, e.g., a connector 115 which is secured to drive shaft 105 and inner tube 25. Preferably connector 115 is provided with appropriate ports so that the interior of inner tube 25 is in fluid communication with a suction port 120, whereby to provide suction to blade assembly 10.

It should be appreciated that handle assembly 15 shown in FIG. 1 is provided by way of example but not limitation, and other handle assemblies may be used in conjunction with blade assembly 10.

FIGS. 11-14 show alternative configurations for outer tube 20 and its window 50.

Figure 11:
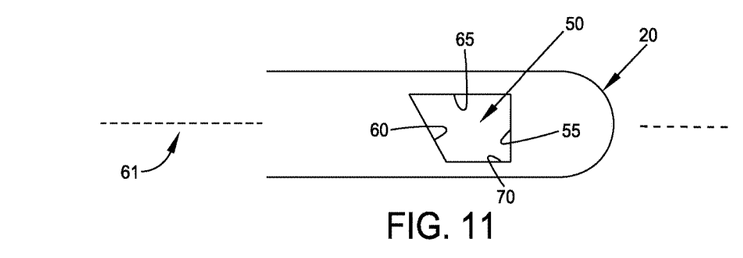
FIGS. 11-14 are schematic views showing alternative constructions for the outer tube of the blade assembly.

More particularly, in FIG. 11, window 50 is constructed so that its leading edge 55 extends perpendicular to the longitudinal axis of outer tube 25 and its trailing edge 60 is canted relative to the longitudinal axis 61 of outer tube 25, with first edge 65 and second edge 70 extending between leading edge 55 and trailing edge 60.

Figure 12:
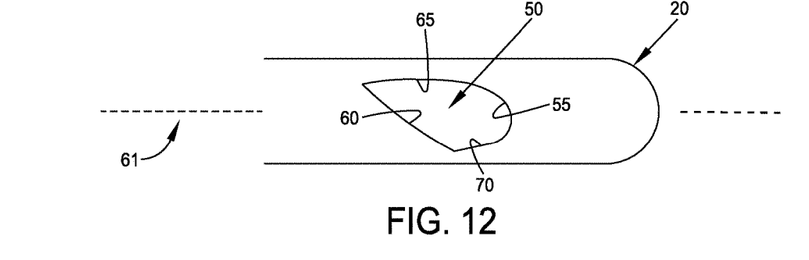

In FIG. 12, window 50 is constructed so that its leading edge 55 and its first edge 65 and second edge 70 combine to form an arcuate surface (i.e., edge), and its trailing edge 60 is canted relative to the longitudinal axis 61 of outer tube 25.

Figure 13:
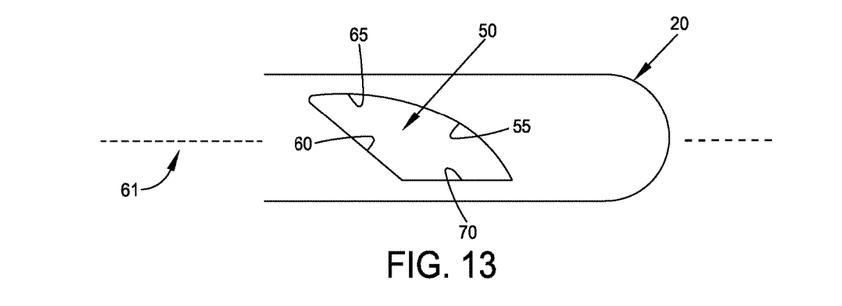

In FIG. 13, window 50 is constructed so that its leading edge 55 and its first edge 65 combine to form an arcuate surface (i.e., edge), its trailing edge 60 is canted relative to the longitudinal axis 61 of outer tube 25, and its second edge 70 extends between leading edge 55 and trailing edge 60.

Figure 14:
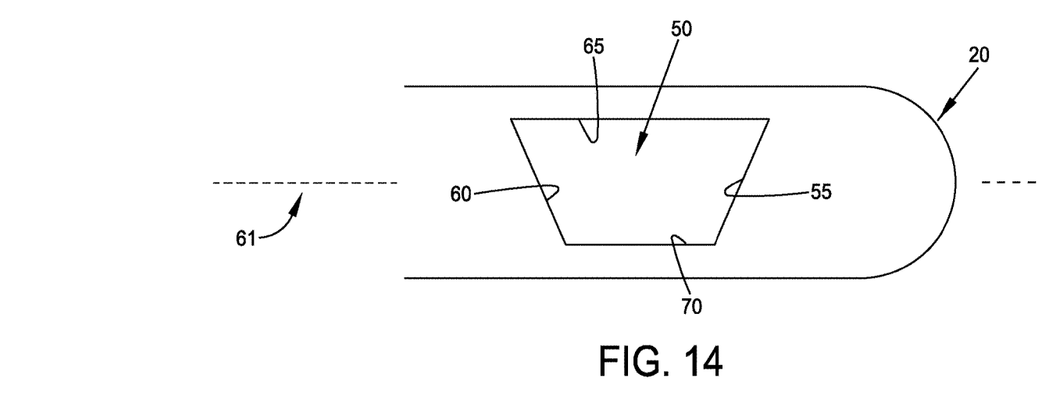

In FIG. 14, window 50 is constructed so that its leading edge 55 and its trailing edge 60 are canted in opposite directions relative to the longitudinal axis of outer tube 25, with first edge 65 and second edge 70 extending between leading edge 55 and trailing edge 60.

Figure 15:
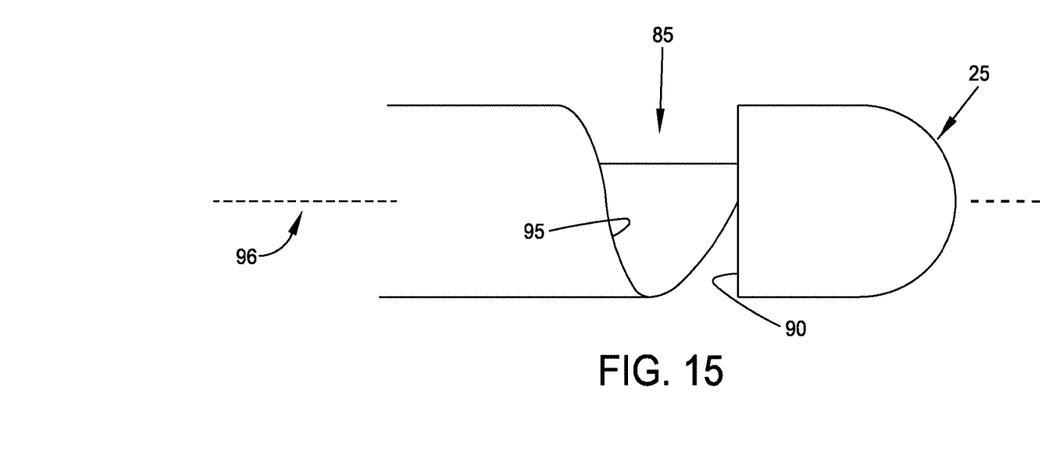
FIG. 15 is a schematic view showing an alternative construction for the inner tube of the blade assembly.

FIG. 15 shows an alternative configuration for inner tube 25 and its opening 85, wherein leading edge 90 extends perpendicular to the longitudinal axis of inner tube 25 and trailing edge 95 has a helical configuration.

The powered shaver of the present invention improves upon the deficiencies of the prior art. Among other things, the new powered cutter provides enlarged window sizes, improved cutting action and superior suction.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A cutting instrument comprising:
   an outer tube comprising a distal end, a proximal end, and a longitudinal axis extending therebetween, said outer tube consisting of a single window formed therein, said window of said outer tube having a leading edge extending between first and second leading edge ends, a trailing edge extending between first and second trailing edge ends, a first side edge connecting said first leading edge end of said leading edge to said first trailing edge end of said trailing edge, and a second side edge connecting said second leading edge end of said leading edge to said second trailing edge end of said trailing edge;
   wherein said first leading edge end of said leading edge of said window of said outer tube is disposed distal to said second leading edge end of said leading edge of said window of said outer tube, and further wherein said first trailing edge end of said trailing edge of said window of said outer tube is disposed distal to said second trailing edge end of said trailing edge of said window of said outer tube; and
   an inner tube rotatably disposed within said outer tube, said inner tube comprising a non-ellipsoidal opening having a leading edge and a trailing edge;
   wherein at least one of said leading edge of said non-ellipsoidal opening of said inner tube and said trailing edge of said non-ellipsoidal opening of said inner tube comprises a canted edge; and
   wherein said window of said outer tube is progressively increasingly blocked, from said leading edge of said window to said trailing edge of said window, during successive phases of rotation of said inner tube within said outer tube, and completely blocked by said inner tube during a phase of the rotation of said inner tube within said outer tube.

2. A cutting instrument according to claim 1 wherein at least one of said canted edge of said non-ellipsoidal opening and said leading edge of said window comprises a helix of constant pitch.

3. A cutting instrument according to claim 1 wherein at least one of said canted edge of said non-ellipsoidal opening and said leading edge of said window comprises a segment of an ellipse.

4. A cutting instrument according to claim 1 wherein, during rotation of said inner tube relative to said outer tube, a scissoring effect is created at one of said leading edge of said window and said trailing edge of said window.

5. A cutting instrument according to claim 1 wherein at least one of said leading edge of said non-ellipsoidal opening and said trailing edge of said non-ellipsoidal opening comprises a helix.

6. A cutting instrument according to claim 1 wherein at least one of said leading edge of said window and said trailing edge of said window comprises a helix.

7. A cutting instrument according to claim 1 wherein said leading edge of said non-ellipsoidal opening, said trailing edge of said non-ellipsoidal opening, said leading edge of said window and said trailing edge of said window all comprise a helix.

8. A cutting instrument according to claim 7 wherein at least one of said leading edge of said non-ellipsoidal opening and said trailing edge of said non-ellipsoidal opening comprises a different pitch than at least one of said leading edge of said window and said trailing edge of said window.

9. A cutting instrument according to claim 1 wherein said at least one canted edge of said non-ellipsoidal opening and said leading edge of said window are canted in the same direction of turn.

10. A cutting instrument comprising:
an outer tube comprising a distal end, a proximal end, and a longitudinal axis extending therebetween, said outer tube consisting of a single window formed therein, said single window of said outer tube having a leading edge extending between first and second leading edge ends, a trailing edge extending between first and second trailing edge ends, a first side edge connecting said first leading edge end of said leading edge to said first trailing edge end of said trailing edge, and a second side edge connecting said second leading edge end of said leading edge to said second trailing edge end of said trailing edge;
wherein said first leading edge end of said leading edge of said window of said outer tube is disposed distal to said second leading edge end of said leading edge of said window of said outer tube, and further wherein said first trailing edge end of said trailing edge of said window of said outer tube is disposed distal to said second trailing edge end of said trailing edge of said window of said outer tube; and
an inner tube rotatably disposed within said outer tube, said inner tube comprising a non-ellipsoidal opening having a leading edge and a trailing edge;
wherein at least one of said leading edge of said non-ellipsoidal opening of said inner tube and said trailing edge of said non-ellipsoidal opening of said inner tube comprises a canted edge, and at least one of said leading edge of said window of said outer tube and said trailing edge of said window of said outer tube comprises a canted edge;
wherein said at least one canted edge of said non-ellipsoidal opening of said inner tube and said at least one canted edge of said window of said outer tube are canted in the same direction of turn; and
wherein said window of said outer tube is progressively increasingly blocked, from said leading edge of said window to said trailing edge of said window, during successive phases of rotation of said inner tube within said outer tube, and completely blocked by said inner tube during a phase of the rotation of said inner tube within said outer tube.

11. A cutting instrument according to claim 10 wherein said at least one canted edge of said non-ellipsoidal opening comprises a helix of constant pitch, and further wherein said at least one canted edge of said window comprises a helix of constant pitch.

12. A cutting instrument according to claim 10 wherein said at least one canted edge of said window comprises a segment of an ellipse.

13. A cutting instrument according to claim 10 wherein, during rotation of said inner tube relative to said outer tube, a scissoring effect is created at one of said leading edge of said non-ellipsoidal opening and said trailing edge of said non-ellipsoidal opening.

14. A cutting instrument according to claim 10 wherein, during rotation of said inner tube relative to said outer tube, a scissoring effect is created at one of said leading edge of said window and said trailing edge of said window.

15. A cutting instrument according to claim 10 wherein at least one of said leading edge of said non-ellipsoidal opening and said trailing edge of said non-ellipsoidal opening comprises a helix.

16. A cutting instrument according to claim 10 wherein at least one of said leading edge of said window and said trailing edge of said window comprises a helix.

17. A cutting instrument according to claim 10 wherein said leading edge of said non-ellipsoidal opening, said trailing edge of said non-ellipsoidal opening, said leading edge of said window and said trailing edge of said window all comprise a helix.

18. A cutting instrument according to claim 17 wherein at least one of said leading edge of said non-ellipsoidal opening and said trailing edge of said non-ellipsoidal opening comprises a different pitch than at least one of said leading edge of said window and said trailing edge of said window.

19. A cutting instrument according to claim 10 wherein said window of said outer tube is adapted to be completely blocked by said inner tube during a phase of the rotation of said inner tube within said outer tube.

20. A method for cutting an object, the method comprising:
providing a cutting instrument comprising:
an outer tube comprising a distal end, a proximal end, and a longitudinal axis extending therebetween, said outer tube consisting of a single window formed therein, said window of said outer tube having a leading edge extending between first and second leading edge ends, a trailing edge extending between first and second trailing edge ends, a first side edge connecting said first leading edge end of said leading edge to said first trailing edge end of said trailing edge, and a second side edge connecting said second leading edge end of said leading edge to said second trailing edge end of said trailing edge;
wherein said first leading edge end of said leading edge of said window of said outer tube is disposed distal to said second leading edge end of said leading edge of said window of said outer tube, and further wherein said first trailing edge end of said trailing edge of said window of said outer tube is disposed distal to said second trailing edge end of said trailing edge of said window of said outer tube; and
an inner tube rotatably disposed within said outer tube, said inner tube comprising a non-ellipsoidal opening having a leading edge and a trailing edge;
wherein at least one of said leading edge of said non-ellipsoidal opening of said inner tube and said trailing edge of said non-ellipsoidal opening of said inner tube comprises a canted edge; and wherein said window of said outer tube is progressively increasingly blocked, from said leading edge of said window to said trailing edge of said window, during successive phases of rotation of said inner tube within said outer tube, and completely blocked by said inner tube during a phase of the rotation of said inner tube within said outer tube;

positioning the object in said window of said outer tube; and rotating said inner tube within said outer tube.

* * * * *